US008486350B2

(12) United States Patent
Nakajima et al.

(10) Patent No.: US 8,486,350 B2
(45) Date of Patent: Jul. 16, 2013

(54) MICROCHIP, MICROCHIP LIQUID SUPPLY SYSTEM, AND MICROCHIP LIQUID SUPPLY METHOD

(75) Inventors: Akihisa Nakajima, Tama (JP); Kusunoki Higashino, Osaka (JP); Yasuhiro Sando, Amagasaki (JP); Youichi Aoki, Hachioji (JP)

(73) Assignee: Konica Minolta Medical & Graphic, Inc. (JP)

( * ) Notice: Subject to any disclaimer, the term of this patent is extended or adjusted under 35 U.S.C. 154(b) by 204 days.

(21) Appl. No.: 12/991,354

(22) PCT Filed: May 1, 2009

(86) PCT No.: PCT/JP2009/058560
§ 371 (c)(1), (2), (4) Date: Jan. 28, 2011

(87) PCT Pub. No.: WO2009/136600
PCT Pub. Date: Nov. 12, 2009

(65) Prior Publication Data

US 2011/0147408 A1 Jun. 23, 2011

(30) Foreign Application Priority Data

May 9, 2008 (JP) ................................ 2008-123144

(51) Int. Cl.
*G01N 15/06* (2006.01)
*G01N 33/00* (2006.01)
*G01N 33/48* (2006.01)

(52) U.S. Cl.
USPC ............ 422/503; 422/50; 422/68.1; 422/502; 422/504; 436/43

(58) Field of Classification Search
USPC ............ 422/50, 68.1, 502, 503, 504; 436/43, 436/180
See application file for complete search history.

(56) References Cited

U.S. PATENT DOCUMENTS 5,764,356 A 6/1998 Iwase et al.
7,364,647 B2 * 4/2008 Paul et al. .................... 204/600

(Continued)

FOREIGN PATENT DOCUMENTS

CA 2189907 A1 5/1997
CA 2439627 A 9/2002

(Continued)

OTHER PUBLICATIONS

Comments and Responses of International Searching Authority for International Application No. PCT/JP2009/058560 with English translation.

(Continued)

*Primary Examiner* — Brian J Sines
(74) *Attorney, Agent, or Firm* — Cantor Colburn LLP

(57) ABSTRACT

Provided is a microchip which is capable of determining the quantity of the liquid in the chip and dividing the liquid, and has a relatively simple flow passage structure. In the microchip liquid supply system, a portion of the liquid in an upstream passage among the liquid injected into a first flow passage is supplied from a liquid discharge passage by operating a suction pump connected to a liquid supply passage in such a state that an air vent hole is closed. Thereafter, the suction pump is operated with the air vent hole closed, whereby a portion of the liquid in a quantity determination passage among the liquid injected into the first flow passage is supplied from a liquid supply passage.

2 Claims, 10 Drawing Sheets

U.S. PATENT DOCUMENTS

| | | | | |
|---|---|---|---|---|
| 7,731,907 | B2 * | 6/2010 | Ballhorn et al. | 422/504 |
| 8,323,985 | B2 * | 12/2012 | Wixforth et al. | 436/180 |
| 2002/0142481 | A1 | 10/2002 | Andersson et al. | |
| 2003/0198576 | A1 | 10/2003 | Coyne et al. | |
| 2003/0210607 | A1 | 11/2003 | Gilbert et al. | |
| 2004/0121450 | A1 | 6/2004 | Pugia et al. | |
| 2004/0209381 | A1 | 10/2004 | Peters et al. | |
| 2007/0297949 | A1 | 12/2007 | Wu et al. | |

FOREIGN PATENT DOCUMENTS

| | | | |
|---|---|---|---|
| CN | 1524619 | A | 9/2004 |
| CN | 101297200 | A | 10/2008 |
| DE | 10302721 | A1 | 8/2004 |
| EP | 0774657 | A2 | 5/1997 |
| EP | 1440732 | A1 | 7/2004 |
| EP | 1942347 | A1 | 7/2008 |
| JP | 9-196739 | A | 7/1997 |
| JP | 2000-514928 | A | 11/2000 |
| JP | 2002-357616 | A | 12/2002 |
| JP | 2004-28589 | A | 1/2004 |
| JP | 2004-226412 | A | 8/2004 |
| JP | 2004-529336 | A | 9/2004 |
| JP | 2005-195561 | A | 7/2005 |
| JP | 2006-23209 | A | 1/2006 |
| JP | 2006-78276 | A | 3/2006 |
| JP | 2006-511810 | A | 4/2006 |
| JP | 2008-101984 | A | 5/2008 |
| WO | 98/53311 | A2 | 11/1998 |
| WO | 02/075312 | A1 | 9/2002 |
| WO | 2004/061414 | A2 | 7/2004 |
| WO | 2007/049534 | A1 | 5/2007 |

OTHER PUBLICATIONS

International Search Report for International Application No. PCT/JP2009/058560 mailed Jun. 23, 2009 with English translation.

Juncker D. et al., "Autonomous Microfluidic Capillary System", Analytical Chemistry, American Chemical Society, US, vol. 74, No. 24, Dec. 15, 2002, pp. 6139-6144.

The Extended European Search Report for European Patent Application No. 09742724.9-1270 dated Dec. 23, 2011.

* cited by examiner

MICROCHIP, MICROCHIP LIQUID SUPPLY SYSTEM, AND MICROCHIP LIQUID SUPPLY METHOD

This is a U.S. national stage application of International Application No. PCT/JP2009/058560, filed on 1 May 2009. Priority under 35 U.S.C. §119(a) and 35 U.S.C. §365(b) is claimed from Japanese Application No. 2008-123144 filed 9 May 2008, the disclosure of which is also incorporated herein by reference.

TECHNICAL FIELD

The present invention relates to a microchip which has minute flow passages to feed (supply) liquid.

BACKGROUND ART

In recent years, with the employment of micromachine techniques and ultra microfabrication techniques, developed is a system in which conventional apparatus to conduct sample preparation, chemical analyses, chemosynthesis, etc. and means (for example, pumps, valves, flow passages, sensors, etc.) are miniaturized so as to be integrated into a single tip (for example, Patent Document 1). This system is also called μ-TAS (Micro Total Analysis System) with which a sample (for example, the urine of a person who undergoes an examination, saliva, extracted solution in which blood is subjected to DNA treatment, etc.) and reagents are mixed in a member called a microchip and the characteristic of the sample is examined by the detection of the reaction of the mixture.

In the microchip, groove fabrication is conducted for a substrate made of a resin material or glass material by a photolithographic process (a process producing grooves by etching a pattern image with chemicals) or the application of laser beams such that the substrate is provided with minute flow passage to allow regents and samples to flow and storage sections to storage reagents. Various patterns of minute flow passage and storage sections are proposed (for example, Patent Document 1).

At the time of investigating the characteristic of a sample by the use of these microchips, liquids such as reagents and samples stored in a microchip are fed to flow passages by micro pumps and the like so that reagents and samples are made to react in the flow passages and led to a detected section to detect the characteristic. In the detected section, object substances are detected by for example, an optical detecting method.

In the microchip, liquids in a slight amount are mixed with a predetermined mixture ratio in a minute flow passage, and then the liquids are made to perform reaction. In such a case, in order to administrate a mixture ratio of the both liquids with sufficient accuracy, the quantification of a liquid becomes very important. For such a request, generally, liquid is quantified by the use of a micropipette and the like and the quantified liquid component is injected into the microchip. However, with such a method, since there is fear of injection leakage, there is a problem that the injected amount is not accurate. In addition, there is a problem that since it is necessary to quantify a required reagent by only the required number of liquid components, the quantification becomes complicate.

For such problems, Patent Document 2 discloses a slight amount liquid controlling mechanism in which a liquid is drawn by a capillary action from a first flow passage to an inside of a third flow passage communicating between the first flow passage and a second flow passage, and then the liquid remaining the first flow passage is removed and liquid droplet with a volume corresponding to the volume of the third flow passage is prepared. Further, Patent Document 3 discloses a method with which a liquid in a chip is shifted with a centrifugal force caused by the rotation of the chip and the liquid is divided and quantified by the volume of a flow passage.

PRIOR ART DOCUMENT

Patent Document

Patent documents 1: Japanese Unexamined Patent Publication No. 2004-28589 official report Patent documents 2: Japanese Unexamined Patent Publication No. 2002-357616 official report Patent documents 3: Japanese Unexamined Patent Publication No. 2000-514928 official report

OUTLINE OF INVENTION

Problems to be Solved by the Invention

However, in the slight amount liquid controlling mechanism disclosed by Patent Document 2, after the third flow passage is filled up with liquid by capillary force, it is difficult to take timing remove the liquid remaining in the first channel, and many sensors are required for the operations. Further, there are following problems: if the configuration of an opening section of a joint section between the third flow passage and the second flow passage is no formed with good accuracy, liquid leakage may be occur, and in the first flow passage, the liquid in the flow passage is wasted too much.

In the method disclosed by Patent document 3, since all flow passages are applied with the centrifugal force, there is a problem that flow passages cannot be controlled independently. Further, since it is necessary to arrange flow passages in consideration of the direction of the centrifugal force, there is a problem that the degree of freedom in arrangement of flow passages is small.

In view of the above-mentioned problems, an object of the present invention is to provide a microchip capable of quantifying and dividing a liquid in its inside with a relatively simple flow passage structure, a microchip liquid (supply) feeding system, and a microchip liquid feeding (supply) method.

Means for Solving the Problems

1. A microchip which divides a predetermined amount of liquid component from an injected liquid and feeds the divided liquid component, the microchip is characterized by comprising:
   - an injection hole through which a liquid is injected;
   - an air vent hole;
   - a first flow passage provided with an upstream passage connected to the injection hole at its upstream side in a liquid feeding direction, a fixed amount passage linked to the upstream passage and provided with a predetermined volume, and a downstream passage linked to the fixed amount passage and connected to the air vent hole at its downstream side in the liquid feeding direction;
   - a discharging passage whose one end is connected to the upstream end of the fixed amount passage and its other end is connected to a suction pump; and a liquid feeding passage whose one end is connected to the downstream end of the fixed amount passage and other end is connected to a suction pump.

2. A microchip which divides a predetermined amount of liquid component from an injected liquid and feeds the divided liquid component, the microchip is characterized by comprising:

an injection hole through which a liquid is injected;

an air vent hole;

a first flow passage provided with an upstream passage connected to the injection hole at its upstream side in a liquid feeding direction, an linking passage liked with the upstream passage and includes a plurality of fixed amount passages which are linked serially and are provided with a predetermined volume, and a downstream passage linked to the linking passage and connected to the air vent hole at its downstream side in the liquid feeding direction;

a discharging passage whose one end is connected to the upstream end of the linking passage and other end is connected to a suction pump; and a plurality of liquid feeding passages whose one ends are connected to a linking section between neighboring fixed amount passages among the plurality of fixed amount passages or the downstream end of a fixed among passage located at the most downstream side in the liquid feeding direction among the plurality of fixed amount passages and other ends are connected to respective suction pumps.

3. A microchip which divides a predetermined amount of liquid component from an injected liquid and feeds the divided liquid component, the microchip is characterized by comprising:

an injection hole through which a liquid is injected;

a liquid storing section liked to the injection hole and to store an injected liquid;

a second flow passage linked to the liquid storing section;

an opening potion;

a first flow passage provided with an upstream passage connected to the opening potion at its upstream side in a liquid feeding direction and connected to the second flow passage on its pathway, an linking passage liked with the upstream passage and includes a plurality of fixed amount passages which are linked serially and are provided with a predetermined volume, and a downstream passage linked to the linking passage and connected to a suction pump at its downstream side in the liquid feeding direction;

a discharging passage whose one end is connected to the upstream end of the linking passage and other end is connected to a suction pump; and a plurality of liquid feeding passages whose one ends are connected to a linking section between neighboring fixed amount passages among the plurality of fixed amount passages or the downstream end of a fixed among passage located at the most downstream side in the liquid feeding direction among the plurality of fixed amount passages and other ends are connected to respective suction pumps.

4. The microchip described in any one of the above 1 to 3 is characterized in that the flow passage sectional area of the linking section between the fixed quantity passages is structured to be smaller than the flow passage sectional area of each fixed quantity passage of the plurality of fixed amount passages.

5. The microchip described in any one of the above 1 to 4 is characterized in that the microchip further comprises a waste liquid storing section, and the discharging section is connected to the waste liquid storing section.

6. A microchip liquid feeding system comprising:

a microchip comprising, an injection hole through which a liquid is injected;

an air vent hole;

a first flow passage provided with an upstream passage connected to the injection hole at its upstream side in a liquid feeding direction, a fixed amount passage linked to the upstream passage and provided with a predetermined volume, and a downstream passage linked to the fixed amount passage and connected to the air vent hole at its downstream side in the liquid feeding direction;

a discharging passage whose one end is connected to the upstream end of the fixed amount passage and its other end is connected to a suction pump; and a liquid feeding passage whose one end is connected to the downstream end of the fixed amount passage and other end is connected to a suction pump;

the suction pumps;

an opening and closing mechanism to open or close the air vent hole; and a control section to control the suction pumps and the opening and closing mechanism;

the microchip liquid feeding system is characterized in that the control section controls such that on the condition that the air vent hole is made to close by the opening and closing mechanism, the suction pump connected to the discharging passage is operated so as to feed a liquid component in the upstream passage among the liquid injected into the first flow passage to the discharging passage, thereafter, on the condition that the air vent hole is closed, the suction pump connected to the liquid feeding passage is operated so as to feed a liquid component in the fixed quantity passage among the liquid injected into the first flow passage to the liquid feeding passage.

7. A microchip liquid feeding system comprising:

a microchip comprising, an injection hole through which a liquid is injected;

an air vent hole;

a first flow passage provided with an upstream passage connected to the injection hole at its upstream side in a liquid feeding direction, an linking passage liked with the upstream passage and includes a plurality of fixed amount passages which are linked serially and are provided with a predetermined volume, and a downstream passage linked to the linking passage and connected to the air vent hole at its downstream side in the liquid feeding direction;

a discharging passage whose one end is connected to the upstream end of the linking passage and other end is connected to a suction pump; and a plurality of liquid feeding passages whose one ends are connected to a linking section between neighboring fixed amount passages among the plurality of fixed amount passages or the downstream end of a fixed among passage located at the most downstream side in the liquid feeding direction among the plurality of fixed amount passages and other ends are connected to respective suction pumps;

the suction pumps;

an opening and closing mechanism to open or close the air vent hole; and a control section to control the suction pumps and the opening and closing mechanism;

the microchip liquid feeding system is characterized in that the control section controls such that on the condition that the air vent hole is made to close by the opening and closing mechanism, the suction pump connected to the discharging passage is operated so as to feed a liquid component in the upstream passage among the liquid injected into the first flow passage to the discharging passage, thereafter, on the condition that the air vent hole is closed, the suction pumps connected to the plurality of liquid feeding passages are operated sequentially so as to feed liquid components sequentially in respective fixed quantity passages in the plurality of liquid feeding passages among the liquid injected into the first flow passage to the liquid feeding passages connected to the respective fixed quantity passages in the order from a fixed quantity passage located at the upstream side in the liquid feeding direction to a fixed quantity passage located at the downstream side in the liquid feeding direction in the linking passage.

8. A microchip liquid feeding system comprising:
  a microchip comprising,
  an injection hole through which a liquid is injected;
  a liquid storing section liked to the injection hole and to store an injected liquid;
  a second flow passage linked to the liquid storing section;
  an opening potion;
  a first flow passage provided with an upstream passage connected to the opening potion at its upstream side in a liquid feeding direction and connected to the second flow passage on its pathway, an linking passage liked with the upstream passage and includes a plurality of fixed amount passages which are linked serially and are provided with a predetermined volume, and a downstream passage linked to the linking passage and connected to a suction pump at its downstream side in the liquid feeding direction;
  a discharging passage whose one end is connected to the upstream end of the linking passage and other end is connected to a suction pump; and
  a plurality of liquid feeding passages whose one ends are connected to a linking section between neighboring fixed amount passages among the plurality of fixed amount passages or the downstream end of a fixed among passage located at the most downstream side in the liquid feeding direction among the plurality of fixed amount passages and other ends are connected to respective suction pumps;
  the suction pumps;
  an opening and closing mechanism to open or close the air vent hole; and
  a control section to control the suction pumps and the opening and closing mechanism;
  the microchip liquid feeding system is characterized in that the control section controls such that on the condition that the opening section is made to close by the opening and closing mechanism, the suction pump connected to the downstream passage is operated so as to feed a liquid in the liquid storing section up to the downstream passage of the first flow passage, subsequently, on the condition that the opening section is made to open, the suction pump connected to the discharging passage is operated so as to feed a liquid component in the upstream passage among the liquid injected into the first flow passage to the discharging passage, thereafter, on the condition that the opening section is made to open, the suction pumps connected to the plurality of liquid feeding passages are operated sequentially so as to feed liquid components sequentially in respective fixed quantity passages in the plurality of liquid feeding passages among the liquid injected into the first flow passage to the liquid feeding passages connected to the respective fixed quantity passages in the order from a fixed quantity passage located at the upstream side in the liquid feeding direction to a fixed quantity passage located at the downstream side in the liquid feeding direction in the linking passage.

9. A liquid feeding method of a microchip which comprises;
  a first flow passage whose both ends are connected to an injection hole and an air vent hole, and provided with an upstream passage connected to the injection hole at its upstream side in a liquid feeding direction, a fixed amount passage linked to the upstream passage and provided with a predetermined volume, and a downstream passage linked to the fixed amount passage and connected to the air vent hole at its downstream side in the liquid feeding direction;
  a discharging passage whose one end is connected to the upstream end of the fixed amount passage and its other end is connected to a suction pump; and
  a liquid feeding passage whose one end is connected to the downstream end of the fixed amount passage and other end is connected to a suction pump;
  the liquid feeding method of the microchip is characterized by comprising:
  a liquid injecting process to inject a liquid from the injection hole to the first flow passage on the condition that the air vent hole is made to open;
  a liquid discharging process to operate the suction pump connected to the discharging passage so as to feed a liquid component in the upstream passage among the liquid injected into the first flow passage to the discharging passage on the condition that the air vent hole is made to close; and
  a liquid feeding process to operate the suction pump connected to the liquid feeding passage so as to feed a liquid component in the fixed quantity passage among the liquid injected into the first flow passage to the liquid feeding passage on the condition that the air vent hole is closed.

10. A liquid feeding method of a microchip which comprises;
  an injection hole through which a liquid is injected;
  a liquid storing section liked to the injection hole and to store an injected liquid;
  a second flow passage linked to the liquid storing section;
  a first flow passage provided with an upstream passage connected to an opening potion at its upstream side in a liquid feeding direction and connected to the second flow passage, an linking passage liked with the upstream passage and includes a plurality of fixed amount passages which are linked serially and are provided with a predetermined volume, and a downstream passage linked to the linking passage and connected to an air vent hole at its downstream side in the liquid feeding direction;
  a discharging passage whose one end is connected to the upstream end of the linking passage and other end is connected to a suction pump; and
  a plurality of liquid feeding passages whose one ends are connected to a linking section between neighboring fixed amount passages among the plurality of fixed amount passages or the downstream end of a fixed among passage located at the most downstream side in the liquid feeding direction among the plurality of fixed amount passages and other ends are connected to respective suction pumps;

the liquid feeding method of the microchip is characterized by comprising:

a liquid injecting process to inject a liquid from the injection hole to the first flow passage on the condition that the air vent hole is made to open;

a liquid discharging process to operate the suction pump connected to the discharging passage so as to feed a liquid component in the upstream passage among the liquid injected into the first flow passage to the discharging passage on the condition that the air vent hole is made to close; and a liquid feeding process to operate the suction pumps connected to the plurality of liquid feeding passages sequentially, on the condition that the air vent hole is made to close, so as to feed liquid components sequentially in respective fixed quantity passages in the plurality of liquid feeding passages among the liquid injected into the first flow passage to the liquid feeding passages connected to the respective fixed quantity passages in order to feed liquid components sequentially in respective fixed quantity passages in the order from a fixed quantity passage located at the upstream side in the liquid feeding direction to a fixed quantity passage located at the downstream side in the liquid feeding direction in the linking passage.

11. A liquid feeding method of a microchip which comprises;

an injection hole through which a liquid is injected;

a liquid storing section liked to the injection hole and to store an injected liquid;

a second flow passage linked to the liquid storing section;

an opening section;

a first flow passage provided with an upstream passage connected to the opening potion at its upstream side in a liquid feeding direction and connected to the second flow passage on its pathway, an linking passage liked with the upstream passage and includes a plurality of fixed amount passages which are linked serially and are provided with a predetermined volume, and a downstream passage linked to the linking passage and connected to an air vent hole at its downstream side in the liquid feeding direction;

a discharging passage whose one end is connected to the upstream end of the linking passage and other end is connected to a suction pump; and a plurality of liquid feeding passages whose one ends are connected to a linking section between neighboring fixed amount passages among the plurality of fixed amount passages or the downstream end of a fixed among passage located at the most downstream side in the liquid feeding direction among the plurality of fixed amount passages and other ends are connected to respective suction pumps;

the liquid feeding method of the microchip is characterized by comprising:

an initial process to inject a liquid from the injection hole to the liquid storing section on the condition that the air vent hole is made to open;

a liquid injecting process to operate the suction pump connected to the downstream passage so as to inject a liquid from the liquid storing section up to the downstream passage on the first flow passage on the condition that the opening section is made to close;

a liquid discharging process to operate the suction pump connected to the discharging passage so as to feed a liquid component in the upstream passage among the liquid injected into the first flow passage to the discharging passage on the condition that the opening section is made to open; and a liquid feeding process to operate the suction pumps connected to the plurality of liquid feeding passages sequentially, on the condition that the opening section is made to open, so as to feed liquid components sequentially in respective fixed quantity passages in the plurality of liquid feeding passages among the liquid injected into the first flow passage to the liquid feeding passages connected to the respective fixed quantity passages in the order from a fixed quantity passage located at the upstream side in the liquid feeding direction to a fixed quantity passage located at the downstream side in the liquid feeding direction in the linking passage.

Effect of the Invention

It becomes possible to provide a microchip capable of quantifying and dividing a liquid in its inside with a relatively simple flow passage structure.

EMBODIMENT FOR CARRYING OUT THE INVENTION

Although the present invention will be explained based on embodiments, the present invention is not restricted to these embodiments.

In this specification, although a "microchip" is a chip in a micro total analyzing system used for various applications, such as synthesis and examination, a microchip used for an examination particularly for biological material may be called an "inspection chip". A "minute flow passage" means in a narrow sense only a flow passage section with a narrow width except a constructing section which may be formed with a wide width. However, the minute flow passage" means in a broad sense a series of flow passages including such a constructing section. A fluid which flows through the inside of a communicating minute flow passage may be a liquid practically in many cases, and, concretely, the fluid correspond to various kinds of reagents, a sample liquid, a modified agent liquid, a cleaning liquid, a driving liquid, and the like.

The present invention is applicable to a reaction detecting apparatus which employs a microchip in addition to the application of a microchip.

Hereafter, an embodiment of the present invention will be described with reference to the drawings.

[One Example of a Microchip]

First, one example of a microchip 1 relating to the first embodiment of the present invention will be explained with reference to FIG. 1.

Figure 1A:
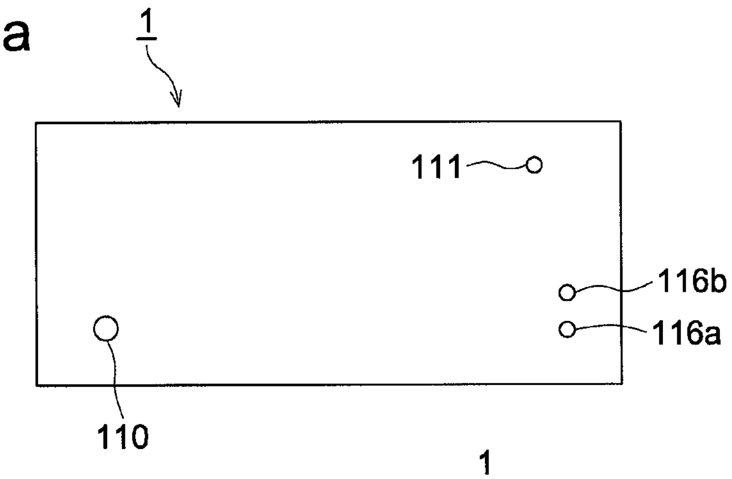
FIG. 1*a* is a top view of a microchip 1.
Figure 1B:
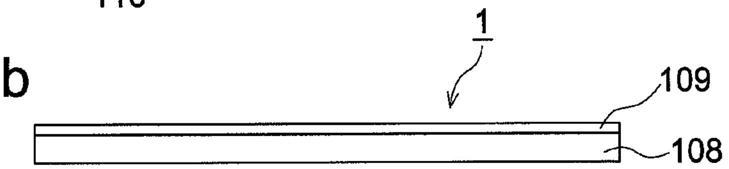
FIG. 1*b* is a side view.

FIG. 1*a* is a top view of the microchip 1, and FIG. 1*b* is a side view. As shown in FIG. 1 (*b*), the microchip 1 is structured with a groove forming substrate 108 and a covering substrate 109 to cover the groove forming substrate 108.

Figure 2:
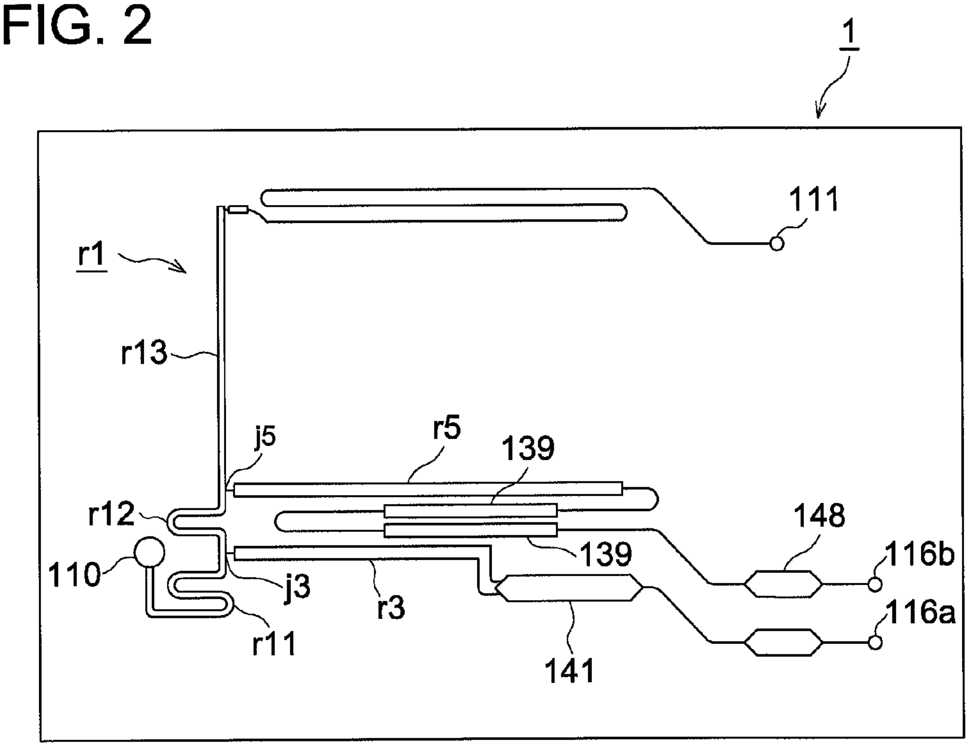
FIG. 2 is a top view when a covering substrate 109 of a microchip 1 is removed.

FIG. 2 is a top view of the microchip 1 when the covering substrate 109 is removed, and is an explanatory drawing of minute flow passages in the microchip 1.

In the microchip 1 according to the embodiment of the present invention, in order to conduct chemical analysis, various examinations, treatment and separation for a sample, chemosynthesis, and the like, minute groove-shaped flow passages (minute flow passage) and functional components (flow passage element) are arranged in a proper pattern in accordance with various purposes. The application of the present invention should not be restricted to the example of the microchip 1 explained in FIG. 2, and the present invention can be applied to a microchip 1 for various purposes.

To the microchip 1, provided are a injection hole 110 into which a liquid is injected, an air vent hole 111, connection holes 116*a* and 116*b* (hereafter, these are collectively called a connection hole 116) to connect with a suction pump, a first minute flow passage r1 (hereafter, merely referred to as a first flow passage r1) whose both ends are connected to the injection hole 110 and the air vent hole 111, a second minute flow passage r3 (hereafter, referred to as a discharging passage r3), and a third minute flow passage r5 (hereafter, referred to as a liquid feeding passage r5).

At the downstream side of the liquid feeding passage r5, provided as a reacting section 139 and a detected section 148. The reacting section 139 heats a liquid having been fed with a heating section (not shown) so as to conduct a gene amplification reaction and other reactions. From the liquid after the reaction, an object substance is detected by a detecting section (not shown), for example, with an optical detecting method and the like. In order to allow optical measurement, a detection portion of the detected section 148 is made of a transparent material, preferably a transparent plastic.

The air vent hole 111 is enabled to open or close by a below-mentioned opening and closing mechanism 56, and the connection hole 116 is connected to a below-mentioned suction pump 71.

The first flow passage r1 is constituted with an upstream passage r11, a fixed quantity passage r12, and a downstream passage r13 in the order from a position near the injection hole 110 which is an upstream side in the liquid feeding direction of a liquid. The upstream passage r11 is linked to the fixed quantity passage r12 at a linking section j3, and the fixed quantity passage r12 is linked to the downstream passage r13 at the linking section j5.

In the fixed quantity passage r12, its flow passage cross-sectional area and length are set such that it has a predetermined amount of volume (for example, 5 μl).

One end of the discharge passage r3 at the upstream side in the liquid feeding direction is connected to the linking section j3 (the upstream end of the fixed quantity passage), and another edge is connected to a suction pump 71 through a connection hole 116*a*. On the pathway of the discharge passage r3, a waste liquid storage section 141 is provided. In the waste liquid storage section 141, an excessive liquid is stored.

One end of the liquid feeding passage r5 at the upstream side in the liquid feeding direction is connected to the linking section j5 (the downstream end of the fixed quantity passage), and another end is connected to a suction pump 71 through a connection hole 116*b*.

The above-mentioned minute flow passages are formed in the groove forming substrate 108 of the microchip 1. The covering substrate 109 is needed to at least come in close contact with the groove forming substrate so as to cover the minutes flow passage, the covering substrate 109 may cover the whole surface of the groove forming substrate.

Figure 3:
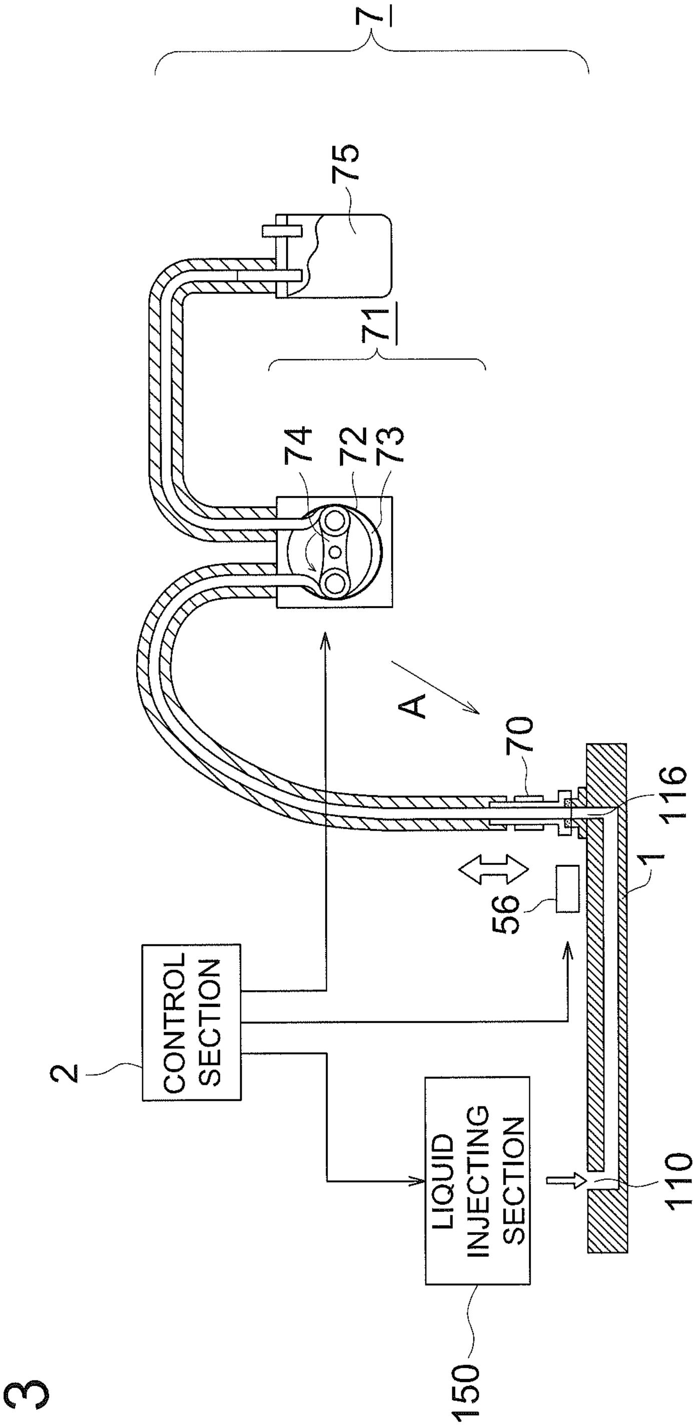
FIG. 3 is a schematic cross sectional view of a microchip liquid feeding system relating to an embodiment
Figure 4:
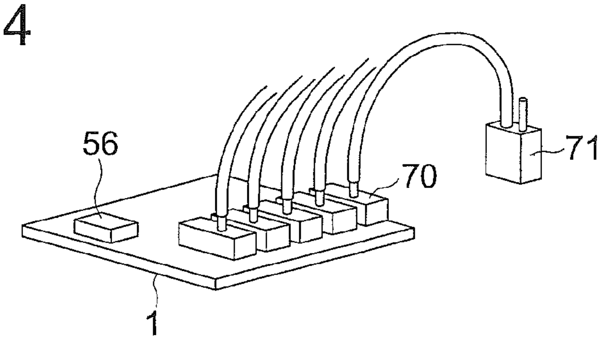
FIG. 4 is a perspective view looked from the A direction of FIG. 3.

FIG. 3 is a schematic cross sectional view of a microchip liquid feeding system according to the first embodiment. FIG. 4 is a perspective view being looked from the A direction in FIG. 3. FIG. 3 shows a condition that the microchip 1 is connected to the suction mechanism 7.

[Suction Mechanism 7]

A suction connecting section 70 of the suction mechanism 7 is connected to the connection hole 116 of the microchip 1. In order to secure a required sealing ability and to prevent gas and a driving liquid from leaking, the suction connecting section 70 is preferably formed by a resin with flexibility such as polytetrafluoroethylene resin and silicone resin.

Numeral 71 is a suction pump to suck in a driving liquid, and in FIG. 3, in order to explain an internal structure, the suction pump is illustrated on a condition that a sealing lid is removed. The suction pump 71 is structured with a tube 73 provided along an inner wall 72, and a rotor 74 capable of rotating while squeezing tube 73. When the rotor 74 rotates counterclockwise as shown in FIG. 3, the tube 73 is pressed onto the inner wall 72, so that a space in the tube 73 moves gradually and air and liquid in the microchip 1 are sucked. The sucked liquid is discharged to a liquid reservoir 75. In this embodiment, the tube pump method utilizing a tube is explained as one example of the suction pump 71. It is not necessary that the suction pump 71 is necessarily such a tube pump type, and it may be the other type pump capable of sucking.

As shown in FIG. 4, a plurality of suction pumps 71 and suction connecting sections 70 are provided corresponding to minutes flow passages, so that it is possible to suck liquid from the respective flow passages independently in the microchip 1.

[Opening and Closing Mechanism 56]

Figure 5:
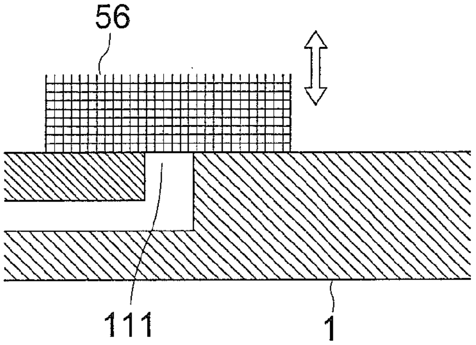
FIG. 5 is an illustration showing a condition that an air vent hole 111 is made to close by an opening and closing mechanism 56.

FIG. 5 is a drawing showing a condition that the air vent hole 111 is closed by the opening and closing mechanism 56. The opening and closing mechanism 56 can shift upward and downward in the vertical direction (the arrowed direction of FIG. 3) in FIG. 5 by a driving section (not shown), and when the air vent hole 111 in the microchip 1 is closed, the opening and closing mechanism 56 shifts downward so as to cover the air vent hole 111.

Figure 6A:
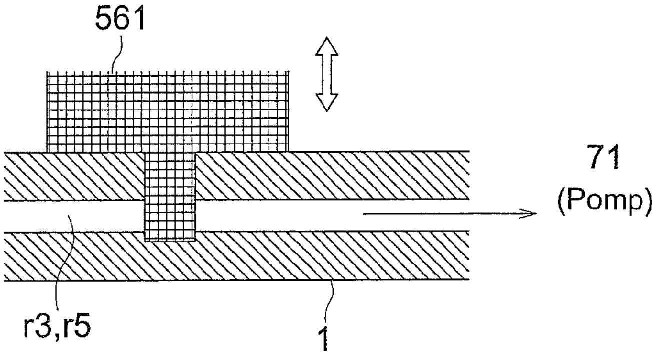
FIG. 6*a* shows a modified example of the opening and closing mechanism.
Figure 6B:
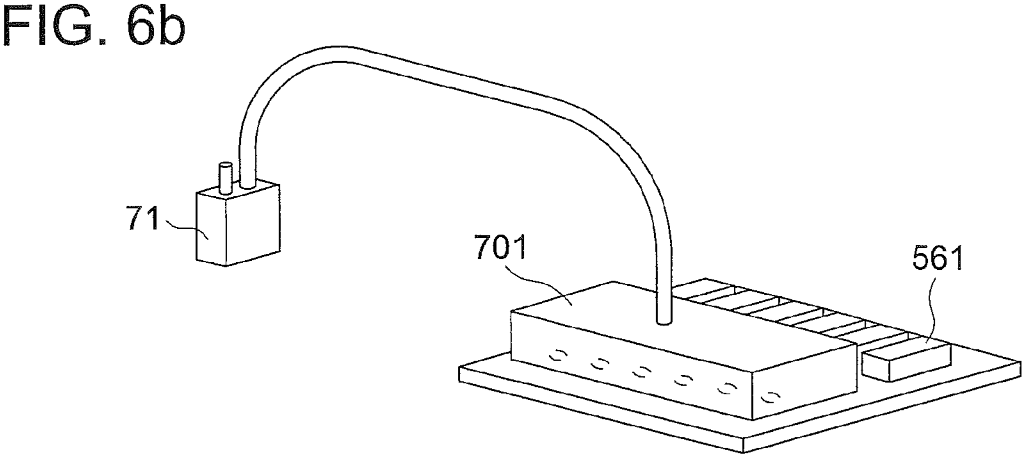
FIG. 6*b* shows a modified example of a suction mechanism 7.

In FIG. 4 and FIG. 5, the explanation was made about the example in which a plurality of suction pumps 71 is provided. However, the present invention should not be restricted to this example. For example, as shown in FIG. 6, tip ends of an opening and closing mechanism 561 corresponding the minute flow passages are inserted in the opening sections 111 so as to conduct cutoff, opening and closing for the minute flow passages, whereby the suction from each inside of a plurality of minute flow passages can be conducted independently with a single suction pump 71 and a single suction connecting section 701.

[Control Section 2]

A control section 2 shown in FIG. 3 is structured with a CPU (central processing unit), RAMs (Random Access Memory), ROMs (Read Only Memory) and the like, and the control section 2 reads out a program memorized in a ROM 96 being a nonvolatile storage section, write it in a RAM 97, and conducts a centralized control in accordance with the program for each section of the liquid injecting section 150, the opening and closing mechanism 56, and the suction pump 71 of a microchip liquid feeding system.

The liquid injecting section 150 stores a liquid in its inside and can inject the liquid in the inside of the microchip 1 through the injection hole 110 by operating a pump.

[Liquid Feeding Method]

Figure 7A:
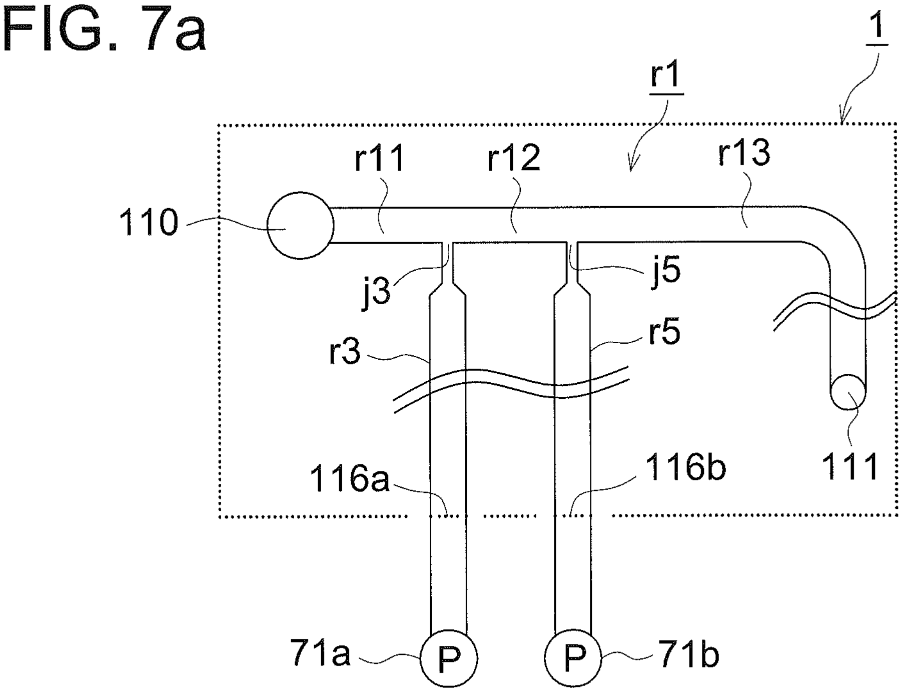
FIG. 7*a* is a schematic diagram of a microchip 1 for explaining an initial state.

With reference to FIG. 7 and FIG. 8, a controlled liquid feeding method by the control section 2 of the microchip 1 in the first embodiment will be explained. FIG. 7 (*a*) is a schematic diagram of a microchip 1 for explaining an initial state. In the condition shown in this diagram, a liquid is not injected into the inside of the microchip 1.

FIG. 7 (*b*) is a schematic diagram of the microchip 1 for explaining a liquid injection process. In "liquid injection process", the microchip 1 is on the condition the the air vent hole 111 is opened by the opening and closing mechanism 56. Each of the suction pump 71*a* at the downstream side of the discharging passage r3 and the suction pump 71*b* at the downstream side of the liquid feeding passage r5 is not operated. On this condition, the downstream side of each of the discharging passage r3 and the liquid feeding passage r5 is in the closed condition. Further, on this condition, the control section 2 injects a liquid from the injection hole 110 by operating the liquid injecting section 150. At this time, since the downstream side of each of the discharging passage r3 and the liquid feeding passage r5 is closed and the air vent hole 111 is open, the liquid flows through the first flow passage r1, without branching at the linking sections j3 and j5. Moreover, the injection amount of the liquid is set to at least an amount with which the liquid reaches the downstream passage r13. As shown in FIG. 7, at the neighborhood of the linking section j3 on the upstream side of the discharging passage r3, since the cross sectional area of a flow passage is narrowed so as to increase flow path resistance than the first flow passage r1, the liquid flowing through the first flow passage r1 cannot proceed easily from the linking section j3 into the discharging passage r3. Also, the neighborhood of the linking section j5 on the upstream side of the liquid feeding passage r5 is structured similarly.

Figure 7B:
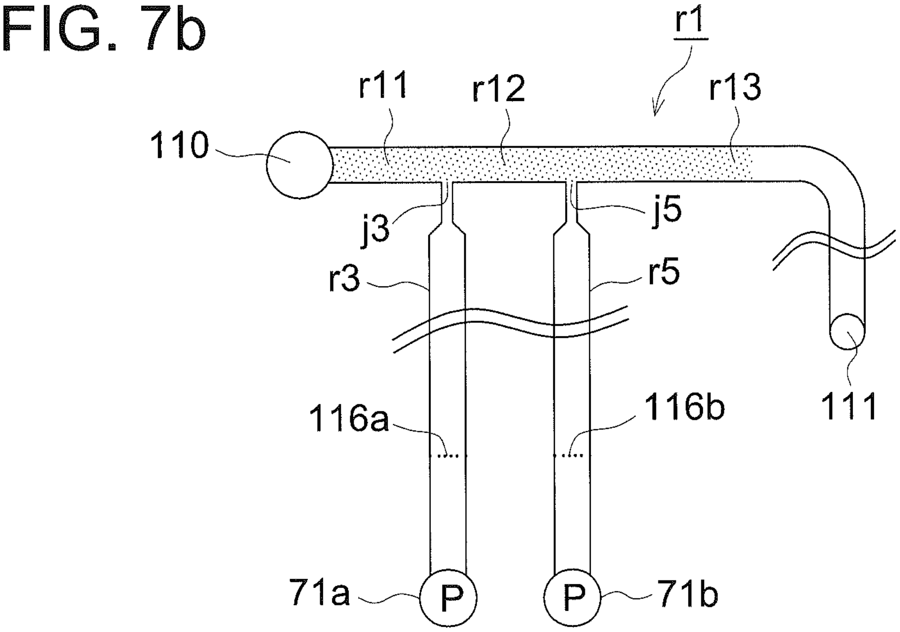
FIG. 7*b* is a schematic diagram of a microchip 1 for explaining a liquid injecting process.
Figure 8A:
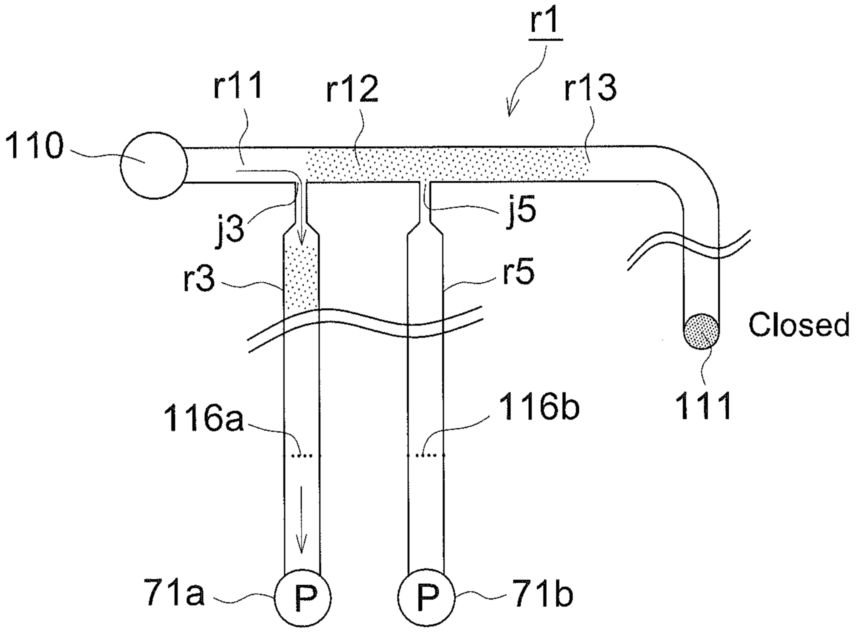
FIG. 8*a* is a schematic diagram of a microchip 1 for explaining a discharging process.

FIG. 8*a* is a schematic diagram of the microchip 1 for explaining a discharging process. In a "discharging process", the control section 2 makes the opening and closing mechanism 56 close the air vent hole 111 (closed). On this condition, the suction pump 71*a* is operated so as to suck the liquid in the upstream passage r11 through the discharging passage r3. With this operation, the liquid component residing in the upstream passage r11 in FIG. 7*b* is fed to the discharging passage r3. Further, on this condition, the liquid component residing in the fixed quantity passage r12 is not shifted. The liquid having been fed to the discharging passage r3 is shifted to the waste liquid storage section 141 at the downstream side. Since the cross sectional area of the flow passage of the waste liquid storage section 141 is larger than that of other sections of the discharging passage r3 except the waste liquid storage section 141, it is possible to prevent the liquid having been stored in the waste liquid storage section 141 from flowing backwards.

Figure 8B:
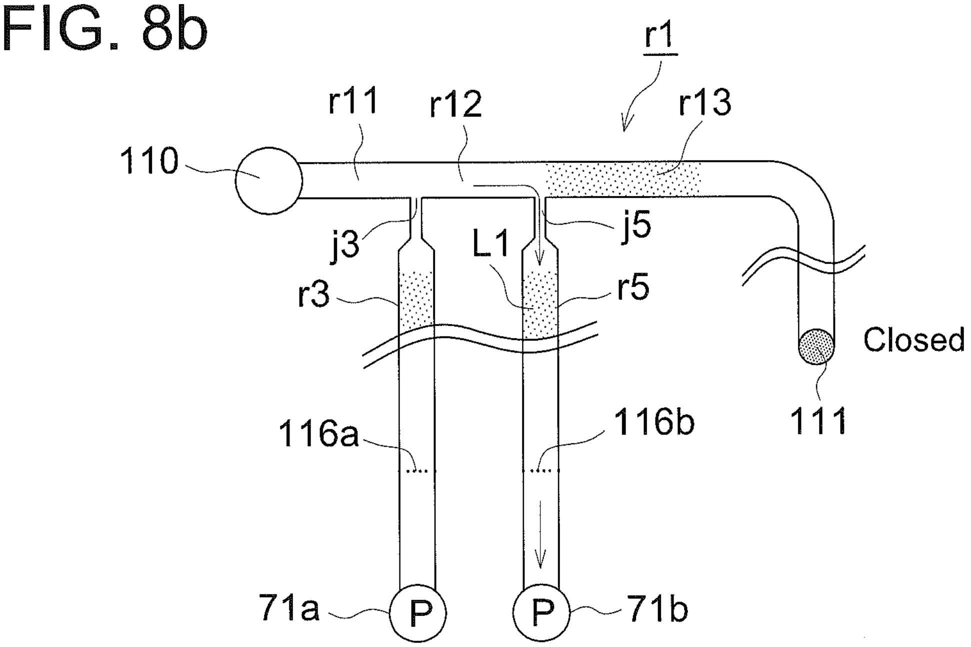
FIG. 8*b* is a schematic diagram explaining a liquid feeding process of a microchip 1.

FIG. 8*b* is a schematic diagram of the microchip 1 for explaining a liquid feeding process. In the "liquid feeding process", the control section 2 operates the suction pump 71*b* connected to the liquid feeding passage r5 on the condition that the air vent hole 111 is closed, so that the liquid component residing in the fixed quantity passage r12 is fed to the liquid feeding passage r5. Since the volume of the fixed quantity passage r12 is set up beforehand to become a predetermined volume (for example, 5 μl), an amount (reference symbol: L1) of liquid fed to the liquid feeding passage r5 can be made to a predetermined volume.

According to this embodiment, with a relatively simple flow passage structure, it becomes possible to quantify and divide a liquid component residing in the inside of the fixed quantity passage of the first flow passage.

The Second Embodiment

Figure 9:
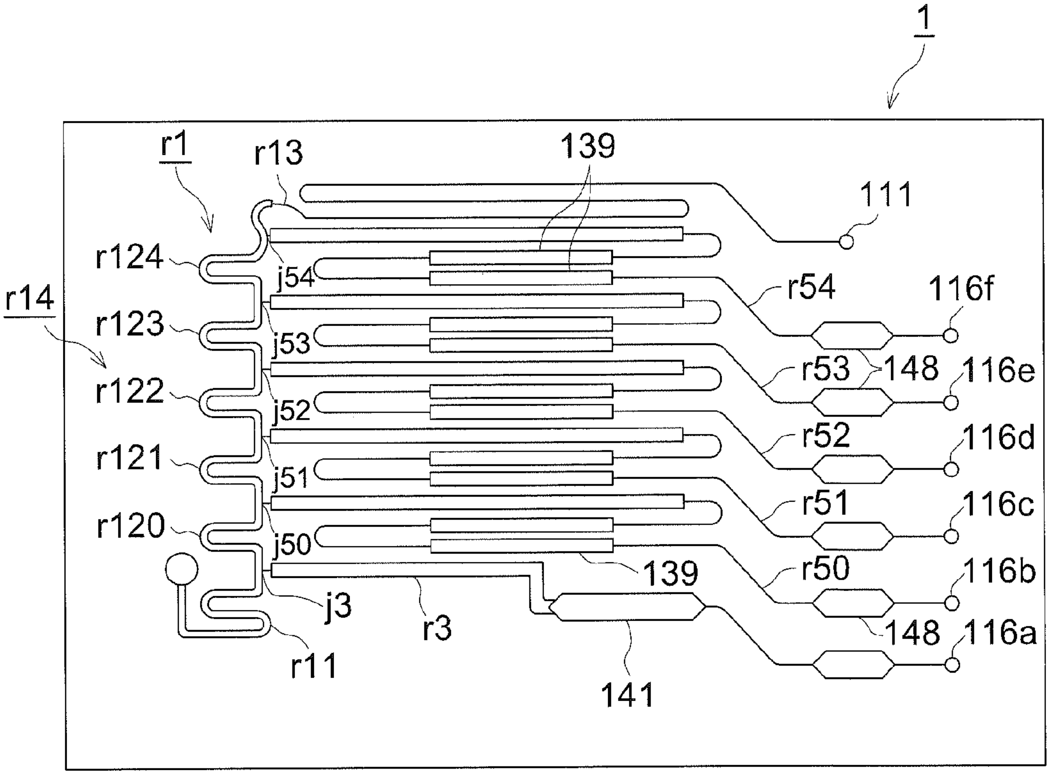
FIG. 9 is explanatory drawing of minute flow passages in the inside of a microchip 1.

With reference to FIG. 9 and FIG. 10, the microchip 1 according to the second embodiment will be explained. In the second embodiment, the arrangement of the minute flow passages and the flow passage elements of the microchip 1 differ from the first embodiment. However, except the arrangement, the second embodiment is the same as the embodiment shown in FIGS. 1 through 8. Therefore, the same reference symbols are provided for the same structures in place of the explanation.

FIG. 9 is an explanatory drawing of minute flow passages in the inside of the microchip 1. In the inside of the microchip 1 shown in this drawing, the first flow passage r1 comprises an upstream passage r11, a connecting passage r14, and a downstream passage r13. The connecting passage r14 is structured with fixed quantity passages r120 to r124 (these are collectively called also fixed quantity passages r12). The fixed quantity passages r120 to r124 are connected to liquid feeding passages r50 to r54 (these are collectively called also liquid feeding passages r5) through linking sections j50 to j54 (these are collectively called also linking sections j5) respectively. The linking sections r50 to r53 correspond to a linking section between neighboring fixed quantity passages. The fixed quantity passage r124 corresponds to a fixed quantity passage of the most downstream side in the liquid feeding direction among a plurality of fixed quantity passages, and the linking section r54 corresponds to the downstream end of the fixed quantity passage r124. The flow passage cross sectional area and length of each of the fixed quantity passages r12 are set up in such a way that the fixed quantity passages r12 have a predetermined amount of volume (for example, 5 μl). In this embodiment, all the fixed quantity passages r12 are designed so as to have the same volume. However, the length and the like are made different in such a way that the fixed quantity passages r12 have respective different volumes.

[Liquid Feeding Method]

With reference to FIG. 10, the controlled liquid feeding method by the control section 2 of the microchip 1 in the second embodiment will be explained.

Figure 10A:
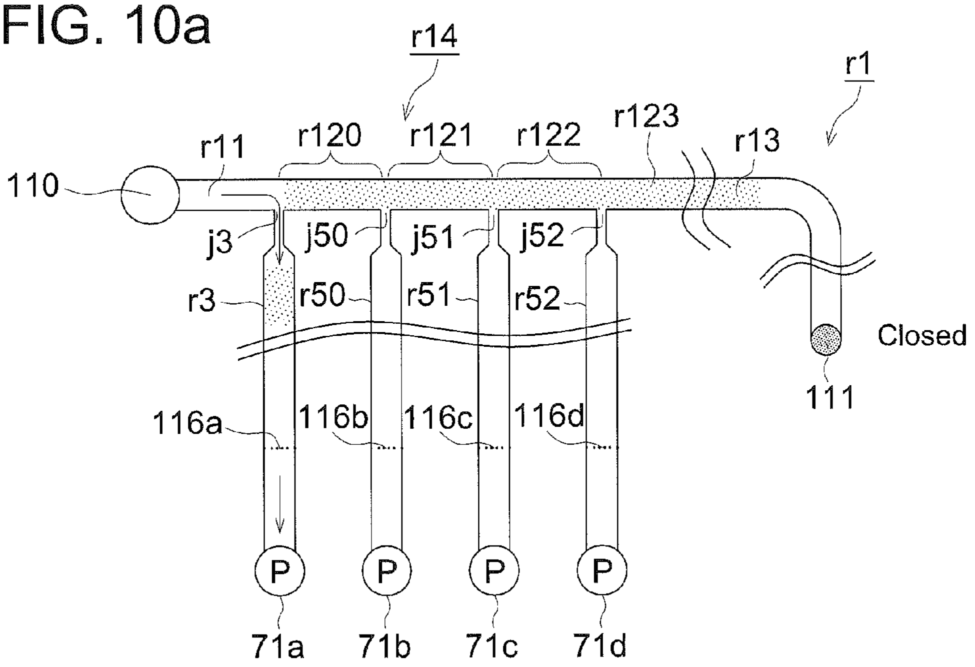
FIG. 10*a* is a schematic diagram of a microchip 1 for explaining a discharging process.

FIG. 10*a* is a schematic diagram of a microchip 1 for explaining a discharging process. FIG. 10 (*b*) is a schematic diagram of a microchip 1 for explaining a liquid feeding process. With reference to the "liquid injection process", since it is the same as the liquid feeding method of the microchip 1 according to the first embodiment having been explained in FIG. 7*b*, an explanation about it is omitted.

In the "discharging process" shown in FIG. 10*a*, the control section 2 makes the opening and closing mechanism 56 close the air vent hole 111 (closed). On this condition, the suction pump 71*a* is operated so as to suck a liquid component residing in the upstream passage r11 through the discharging passage r3. With this operation, the liquid component residing in the upstream passage r11 is fed to the discharging passage r3. Further, on this condition, the liquid component residing in the fixed quantity passage 120 and other connecting passage 14 are not shifted.

Figure 10B:
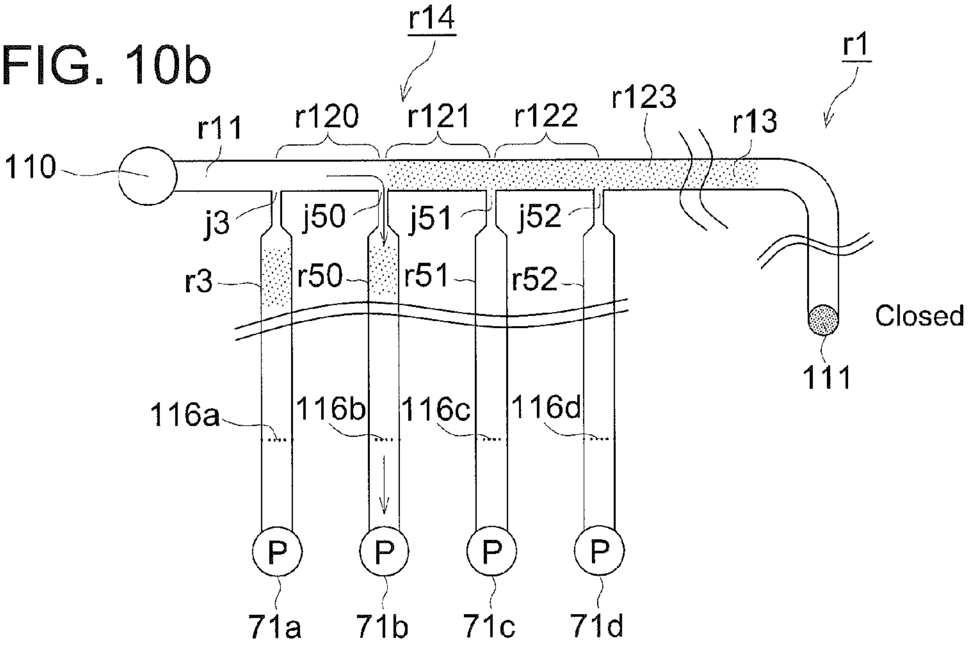
FIG. 10*b* is a schematic diagram of a microchip 1 for explaining a liquid feeding process.

In the "liquid feeding process" shown in FIG. 10*b*, firstly, the liquid component residing in the fixed quantity passage r120 at the most upstream side of the connecting passage r14 is fed to the liquid feeding passage r50 which connects with the linking section j50 (a linking section between neighboring fixed quantity passages) at the downstream. Concretely, on the condition that the air vent hole 111 is closed, the suction pump 71*b* at the downstream side of the liquid feeding passage r50 is operated so as to suck the liquid in the fixed quantity passage r120 through the liquid feeding passage r50. As described above, since the volume of the fixed quantity passage r120 is set up beforehand to become a predetermined volume (for example, 5 μl), the amount of the liquid fed to the liquid feeding passage r50 can be made to a predetermined volume.

Hereafter, suction pumps (71*c*, 71*d*, etc.) connected to plural liquid feeding passages (r51, r52, etc.) respectively, are operated sequentially. With this operation, in the order from the fixed quantity passage at the upstream side in the liquid feeding direction to the fixed quantity passage at the downstream side in the liquid feeding direction on the connecting passage r14, such as in the order of the fixed quantity passage r121, the fixed quantity passage r122, and the fixed quantity passage r123, the predetermined quantity of the liquid in each of the fixed quantity passages r12 is sequentially fed to respective liquid feeding passages r5 connecting with the linking sections j5 at the downstream of the fixed quantity passage r12.

According to this embodiment, with a relatively simple flow passage structure, it becomes possible to quantify and divide a liquid component residing in the inside of the fixed quantity passage of the first flow passage into a plurality of liquid components and to feed the plurality of liquid components respectively.

The Third Embodiment

The microchip 1 relating to the third embodiment will be explained with reference to FIG. 11 and FIG. 12. In the third embodiment, a liquid storage section 140 connected to the injection hole 110 and a second flow passage r2 connected to the liquid storage section 140 at the downstream side are provided, and a pump 71*k* is connected to the downstream side of the discharging passage r3 located at the downstream side of the first flow passage r1. Further, an opening section 111*a* is provided at one end, at the upstream side, of the first flow passage r1. Other structures except the above are the same as the first embodiment and the second embodiment shown in FIGS. 1 through 10. Therefore, the same reference symbols are provided for the same structures in place of the explanation.

Figure 11A:
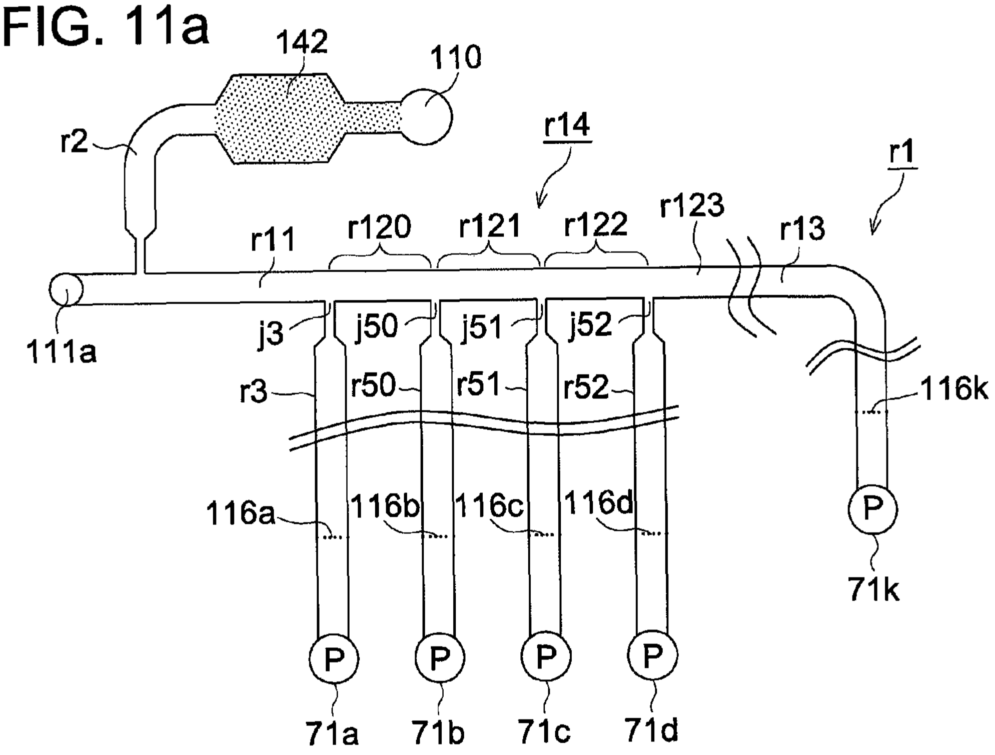
FIG. 11*a* is a schematic diagram of a microchip 1 for explaining an initial state.

FIG. 11*a* is a schematic diagram of the microchip 1 for explaining an initial process. In the situation shown in the above drawing, on the condition that the opening 111*a* is made to open, a liquid is injected into the liquid storage section 140 of the microchip 1 from the injection hole 110.

Figure 11B:
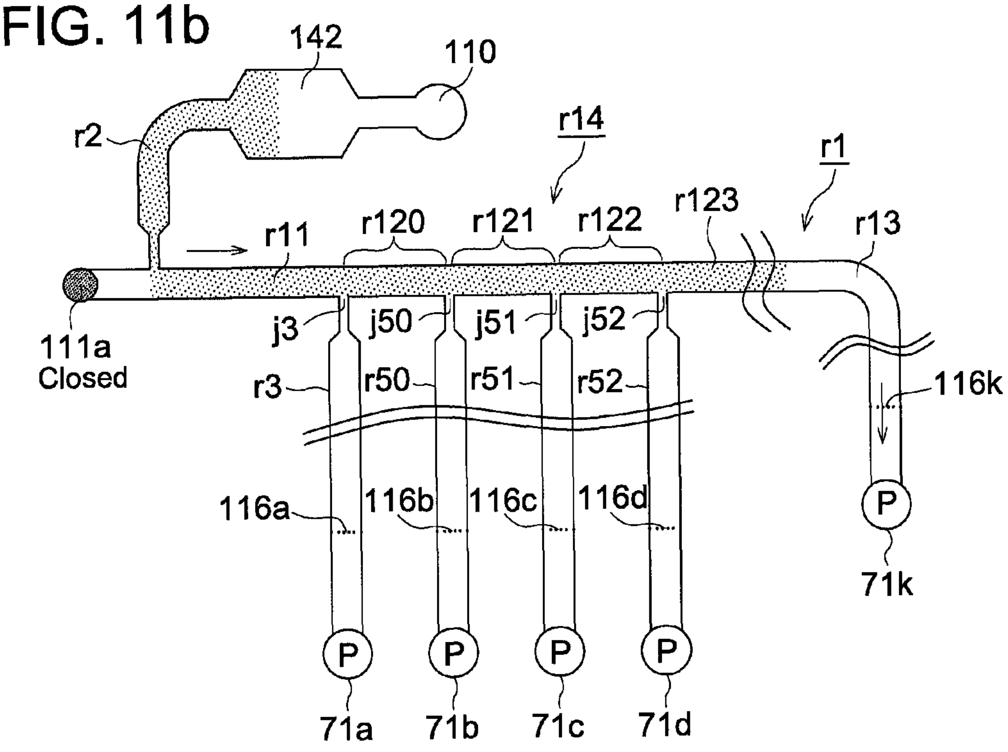
FIG. 11*b* is a schematic diagram of a microchip 1 for explaining a liquid injection process.

FIG. 11 (*b*) is a schematic diagram of the microchip 1 for explaining a liquid injecting process. In the "liquid injection process", the opening 111*a* which was being opened at the initial state is made to close by the opening and closing mechanism 56. Further, any one of the suction pump 71*a* at the downstream side of the discharging passage r3 and the suction pumps 71*b* to 71*d* at the downstream side of the liquid feeding passages r50 to r52 is not operated. On this condition, the downstream side of each of the discharging passage r3 and the liquid feeding passages r50 to r52 is in the closed condition. Under the above condition, the control section 2 operates the suction pump 71*k* so as to feed the liquid from the liquid storage section 140 to at least the upstream passage r11, the connecting passage r14, and the downstream passage r13 on the first flow passage r1. At this time, since the downstream side of each of the discharging passage r3 and the liquid feeding passages r5 (r50 to r52) is closed, the liquid from the liquid from the liquid storage section 140 is fed in the inside of the first flow passage r1 without branching into the linking sections j3 and j5 (j50 to j52).

Figure 12A:
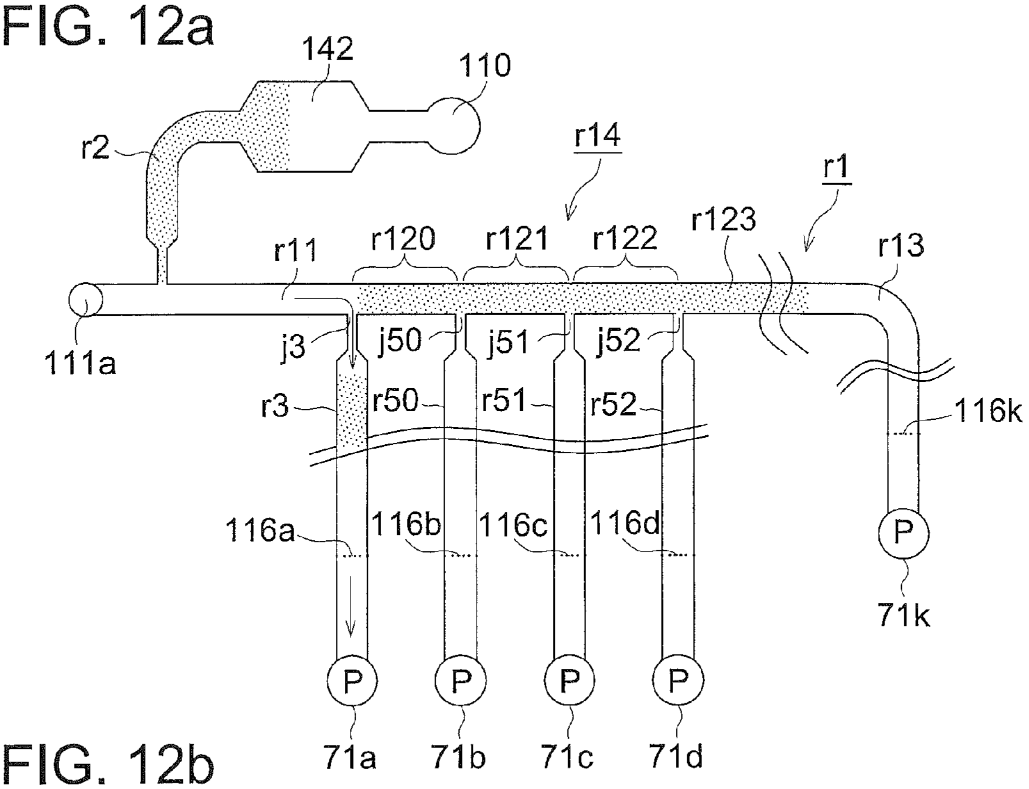
FIG. 12*a* is a schematic diagram of a microchip 1 for explaining a discharging process.
Figure 12B:
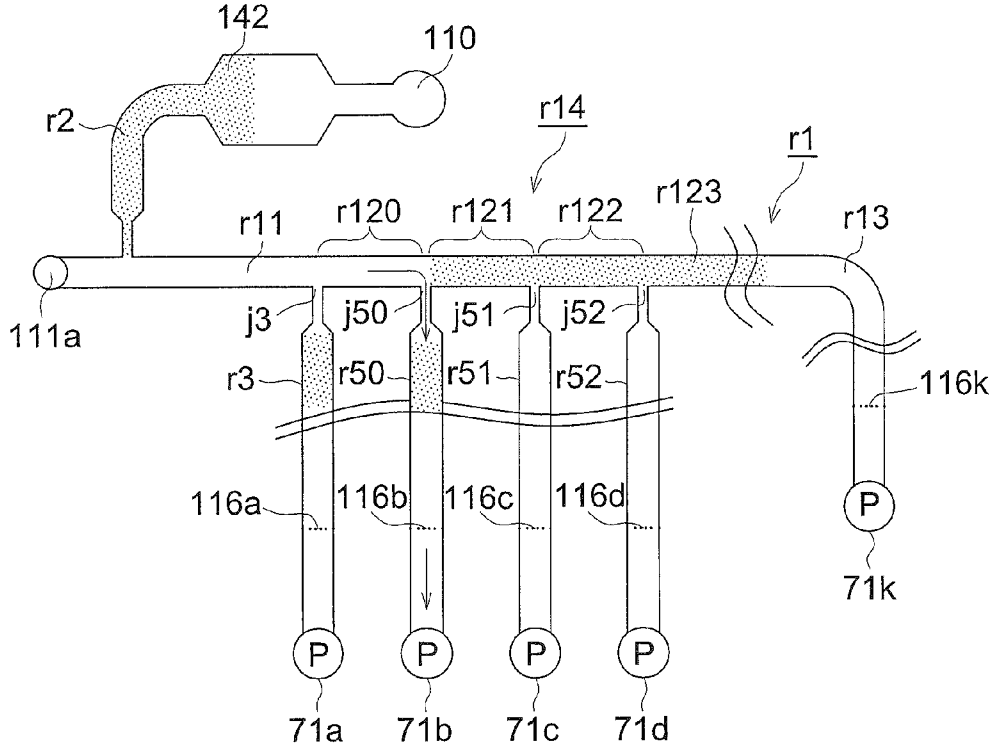
FIG. 12*b* is a schematic diagram of a microchip 1 for explaining a liquid feeding process.

FIG. 12*a* is a schematic diagram of the microchip 1 for explaining a discharging process. FIG. 12*b* is a schematic diagram of the microchip 1 for explaining a liquid feeding process. In the "discharging process" shown in FIG. 12*a*, the control section 2 operates the suction pump 71*a* after the opening 111*a* has been opened by the opening and closing mechanism 56. With this, the liquid component residing in the upstream passage r11 is sucked in the discharging passage r3. On this condition, the liquid in the fixed quantity passage r120, the liquid in the other connecting passages r14 and the liquid in the upstream side than the second flow passage r2 are not shifted.

In the "liquid feeding process" shown in FIG. 12*b*, firstly, the liquid component residing in the fixed quantity passage r120 at the most upstream side of the connecting passage r14 is fed to the liquid feeding passage r50 which connects with the linking section j50 at the downstream. Concretely, on the condition that the air vent hole 111*a* is made to open, the suction pump 71*b* at the downstream side of the liquid feeding passage r50 is operated so as to suck the liquid in the fixed quantity passage r120 through the liquid feeding passage r50. As described above, since the volume of the fixed quantity passage r120 is set up beforehand to become a predetermined volume (for example, 5 μl), the amount of the liquid fed to the liquid feeding passage r50 can be made to a predetermined volume.

Hereafter, suction pumps (71*c*, 71*d*, etc.) connected to plural liquid feeding passages (r51, r52, etc.) respectively, are operated sequentially. With this operation, in the order from the fixed quantity passage at the upstream side in the liquid feeding direction to the fixed quantity passage at the downstream side in the liquid feeding direction on the connecting passage r14, such as in the order of the fixed quantity passage r121, the fixed quantity passage r122, and the fixed quantity passage r123, the predetermined quantity of the liquid in each of the fixed quantity passages r12 is sequentially fed to respective liquid feeding passages r51, r52, etc. connecting with the linking sections j51, j52, etc. at the downstream of the fixed quantity passages r12.

According to this embodiment, with a relatively simple flow passage structure, it becomes possible to quantify and divide a liquid component residing in the inside of the fixed quantity passage of the first flow passage into a plurality of liquid components and to feed the plurality of liquid components respectively.

[Modified Example of a Linking Section]

Figure 13:
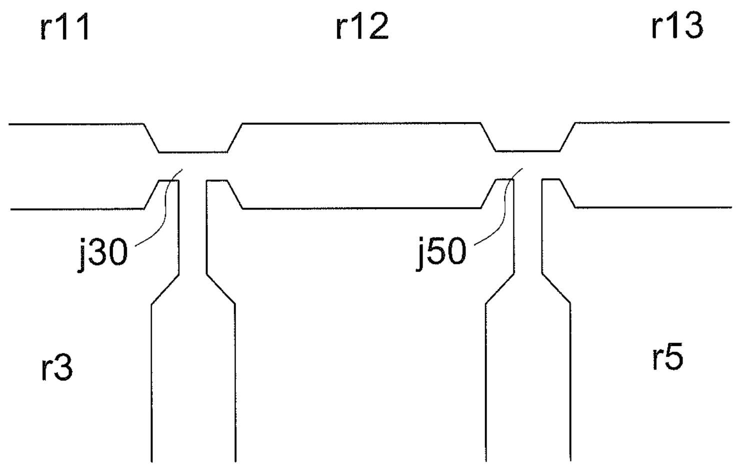
FIG. 13 is an enlarged view of a minute flow passage structure in the vicinity of a fixed quantity passage r12 in the fourth embodiment.

FIG. 13 is an enlarged view of the minute flow passage structure in the vicinity of the fixed quantity passage r12 in the fourth embodiment. In the above drawing, a modified example in the first embodiment shown in the FIG. 7 is explained. However, the similar structure may be applied to the second and third embodiment.

In the fourth embodiment, the flow passage sectional area of the linking section j30 at the upstream side of the fixed quantity passage r12 and the flow passage sectional area of the linking section j50 at the downstream side is made smaller than the flow passage sectional area of the fixed quantity passage r12. In the case that there is variation in suction pressure, the liquid near a linking section may be sucked or may not be sucked due to change in the viscosity of liquid. In order to lessen this effect, as shown in FIG. 13, the flow passage sectional area of the linking sections j30 and j50 is narrowed. With such a structure, it becomes possible to lessen variation in the liquid sucked toward the discharging passage r3 or the liquid feeding passage r5, whereby it becomes possible to increase the accuracy of a fixed quantity.

EXPLANATION OF REFERENCE SYMBOLS r1 Firstflow passage
r11 Upstream passage
r12 Fixed quantity passage
r13 Downstream passage
r3 Discharging passage
j3 Linking section
r5 Liquid feeding passage
j5 Linking section
110 Injection hole
111 Air vent hole
116, 116*a*, and 116*b* Connection hole
71, 71*a* to 71*d* Pump
56, 561 Opening and closing mechanism
141 Waste liquid storage section
142 Liquid storage section
r120 to r124 Fixed quantity passage
r50 to r54 Liquid feeding passage
j50 to j54 Linking section
111*a* Opening section

The invention claimed is:

1. A microchip which divides a predetermined amount of a liquid component from an injected liquid and feeds the divided liquid component, comprising:

a chip body having an injection hole through which a liquid is injected, and an air vent hole;

a first flow passage including an upstream passage connected to the injection hole at an upstream end thereof in a liquid feeding direction, a fixed amount passage linked to the upstream passage and provided with a predetermined volume to store a predetermined amount of a liquid component injected through the upstream passage, and a downstream passage linked to the fixed amount passage and connected to the air vent hole at a downstream end thereof in the liquid feeding direction;

a discharging passage whose one end is connected to the downstream end of the upstream passage and other end is configured to be connected to a suction pump configured to discharge a liquid component residing in the upstream passage through the discharging passage; and a liquid feeding passage whose one end is connected to the downstream end of the fixed amount passage; and a reaction chamber having an inlet port connected to other end of the liquid feeding passage and an outlet port configured to be connected to a suction pump configured to feed the predetermined amount of a liquid component from the fixed amount passage to the reaction chamber.

2. The microchip described in claim 1, further comprising:

a waste liquid storing section for storing a waste liquid, and wherein the discharging section is connected to the waste liquid storing section.

* * * * *